(12) United States Patent
Limpisvasti et al.

(10) Patent No.: US 11,931,057 B2
(45) Date of Patent: Mar. 19, 2024

(54) BENDABLE HANDHELD MEDICAL ACTUATOR

(71) Applicant: ARTHREX, INC., Naples, FL (US)

(72) Inventors: Orr Limpisvasti, Manhattan Beach, CA (US); Ryan Kellar, Naples, FL (US); Jerel Barrera, Seal Beach, CA (US); Robert Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 608 days.

(21) Appl. No.: 17/031,003

(22) Filed: Sep. 24, 2020

(65) Prior Publication Data

US 2022/0087701 A1 Mar. 24, 2022

(51) Int. Cl.
*A61B 17/29* (2006.01)
*A61B 17/28* (2006.01)

(52) U.S. Cl.
CPC ............ *A61B 17/29* (2013.01); *A61B 17/282* (2013.01); *A61B 2017/2905* (2013.01); *A61B 2017/294* (2013.01)

(58) Field of Classification Search
CPC .................. A61B 17/29; A61B 17/282; A61B 2017/2905; A61B 2017/294; A61B 2017/00946; A61B 2017/2901; A61B 2017/2902
See application file for complete search history.

(56) References Cited

U.S. PATENT DOCUMENTS

| | | |
|---|---|---|
| 3,915,169 A | 10/1975 | Mcguire |
| D274,096 S | 5/1984 | Shutt |
| 4,887,593 A | 12/1989 | Wiley et al. |
| 5,013,312 A | 5/1991 | Parins et al. |
| 5,403,305 A | 4/1995 | Sauter et al. |
| 5,464,421 A | 11/1995 | Wortrich |
| 5,582,607 A | 12/1996 | Lackman |
| 6,004,329 A | 12/1999 | Myers et al. |
| 6,093,184 A | 7/2000 | Campbell et al. |
| 6,139,563 A | 10/2000 | Cosgrove et al. |

(Continued)

FOREIGN PATENT DOCUMENTS

| | | |
|---|---|---|
| EP | 1872730 | 5/2011 |
| WO | 2009073577 | 6/2009 |

OTHER PUBLICATIONS

World Intellectual Property Organization, "International Search Report and Written Opinion," issued for international patent application No. PCT/US2021/051252, dated Dec. 30, 2021; document of 13 pages.

*Primary Examiner* — Brooke Labranche
(74) *Attorney, Agent, or Firm* — Greenberg Traurig, LLP; Michael K. Dixon

(57) ABSTRACT

A handheld medical device with a distal implement is disclosed. The handheld rotary medical device may include an inner drive shaft, an elongated, tubular, outer housing encapsulating the inner drive shaft such that the inner drive shaft is positioned within the outer housing. The inner drive shaft may include one or more inner drive shaft bendable sections, and the outer housing may include one or more outer housing bendable sections. The inner drive shaft bendable section may be heated to anneal the material forming the inner drive shaft bendable section such that during use the inner drive shaft bendable section may be bent into a desired position and, once bent, the inner drive shaft bendable section remains in the desired position and does not bind against the elongated, tubular, outer housing.

15 Claims, 4 Drawing Sheets

(56) References Cited

U.S. PATENT DOCUMENTS

| | | |
|---|---|---|
| 6,200,306 B1 | 3/2001 | Klostermeyer |
| 6,231,601 B1 | 5/2001 | Myers et al. |
| 7,229,456 B2 | 6/2007 | Lang et al. |
| D624,652 S | 9/2010 | Carus et al. |
| D641,874 S | 7/2011 | Solingen et al. |
| 9,198,685 B2 | 12/2015 | Edwards et al. |
| 9,370,395 B2 | 6/2016 | Swanson |
| 10,473,144 B2 | 11/2019 | Kupferschmid |
| 2005/0187537 A1 | 8/2005 | Loeb et al. |
| 2007/0049966 A1 | 3/2007 | Bonadio et al. |
| 2008/0221601 A1 | 9/2008 | Huynh et al. |
| 2008/0243031 A1 | 10/2008 | Seibel et al. |
| 2010/0121361 A1 | 5/2010 | Plowe et al. |
| 2011/0276083 A1 | 11/2011 | Shelton et al. |
| 2012/0265175 A1 | 10/2012 | Deflandre et al. |
| 2013/0116693 A1 | 5/2013 | Nelson et al. |

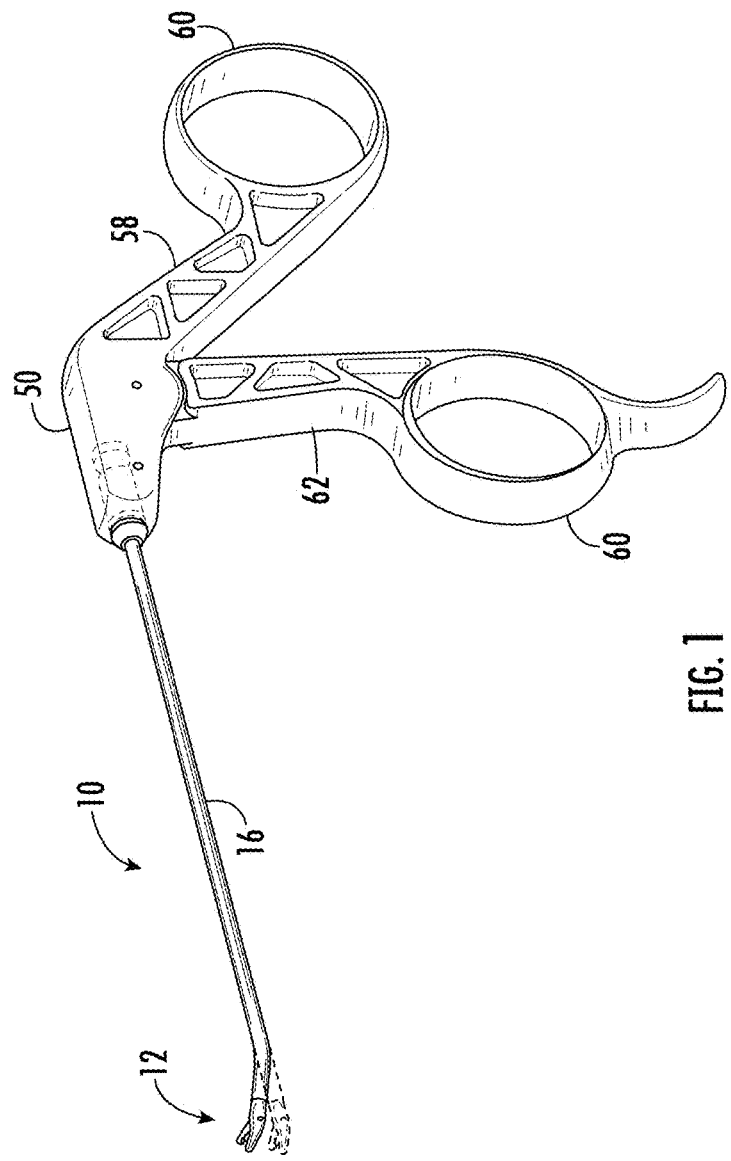
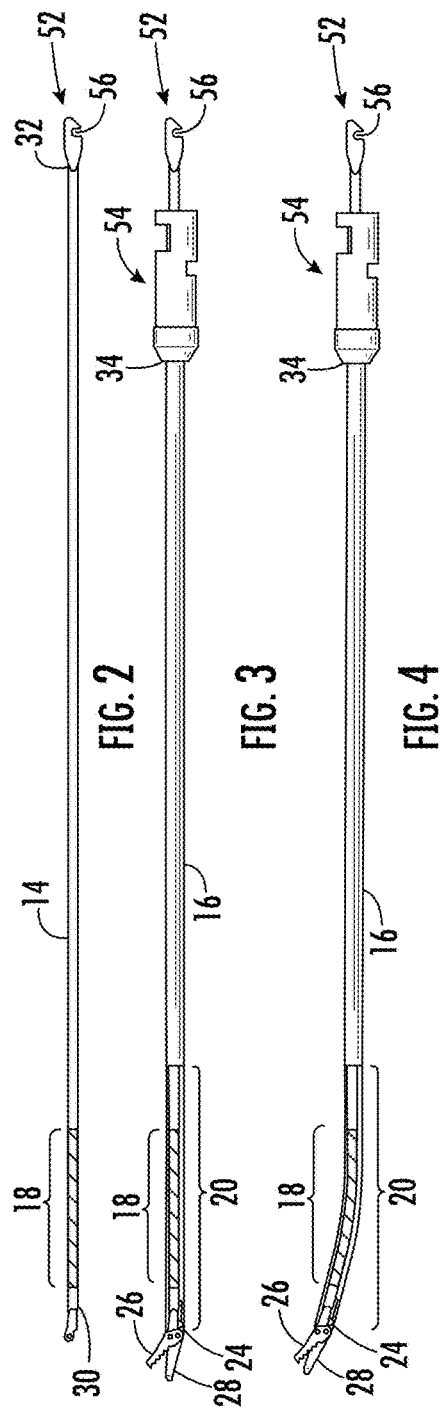
FIG. 1
FIG. 2
FIG. 3
FIG. 4

BENDABLE HANDHELD MEDICAL ACTUATOR

FIELD OF THE INVENTION

The disclosure relates generally to handheld medical device, and more particularly, to handheld, handheld medical devices that are bendable by a surgeon to obtain a desired position for use in a medical procedure.

BACKGROUND

Handheld medical devices often include a distally extending drive shaft positioned within a cylindrical outer housing. The distally extending drive shaft may be configured for rotary motion, axial movement or both depending on the type of attachment on the distal end of the device. The attachment on the distal may be a shaver, burr, jaws and the like configured to remove or grasp soft tissue. Often the inner shaft and outer housing may be bendable to enable a surgeon to bend the shaft and housing into a desired configuration for a particular surgical procedure. Many times, bending the shaft and housing reduces the ease with which the device can be used by causing binding between the shaft and the housing. At times, the binding can be so bad to nearly prevent and substantially limit use of the device. Thus, a need exists for a better solution for a bendable, handheld medical device.

SUMMARY

A handheld medical device with a distal implement is disclosed. The handheld rotary medical device may include an inner drive shaft, an elongated, tubular, outer housing encapsulating the inner drive shaft such that the inner drive shaft is positioned within the outer housing. The inner drive shaft may include one or more inner drive shaft bendable sections, and the outer housing may include one or more outer housing bendable sections. The inner drive shaft bendable section may be heated to anneal the material forming the inner drive shaft bendable section such that during use, the inner drive shaft bendable section may be bent into a desired position and, once bent, the inner drive shaft bendable section remains in the desired position and does not bind against the elongated, tubular, outer housing.

The handheld medical device may include an inner drive shaft, an elongated, tubular, outer housing encapsulating the inner drive shaft such that the inner drive shaft is positioned within the outer housing. The handheld medical device may include an implement at a distal end of the outer housing. The inner drive shaft may include one or more inner drive shaft bendable sections positioned between distal and proximal ends of the inner drive shaft. The outer housing may include one or more outer housing bendable sections positioned between distal and proximal ends of outer housing.

In at least one embodiment, that inner drive shaft bendable section may be more bendable than the outer housing bendable section. The inner drive shaft bendable section may be formed from an annealed material. The inner drive shaft bendable section may be heated before being positioned in or once positioned within the outer housing bendable section. The inner drive shaft bendable section may have a lower flexure modulus than a flexure modulus for the outer housing bendable section. The inner drive shaft bendable section may be more flexible than the at least one outer housing bendable section. The inner drive shaft bendable section may have a lower modulus of elasticity than a modulus or elasticity for the outer housing bendable section.

The inner drive shaft bendable section may be formed within a distal third of the inner drive shaft bendable section. The inner drive shaft bendable section may be formed from a same material as a material forming the outer housing bendable section.

The handheld medical device may include an implement at the distal end of the outer housing may include, but is not limited to having, first and second jaws. The handheld medical device may include a bender configured to bend the inner drive shaft bendable section and the outer housing bendable section. The bender may include first and second arms coupled together via a pivot pin, whereby the first arm includes a first curved shaft receiver and the second arm includes a second curved shaft receiver that is aligned with the first curved shaft receiver.

A method of forming handheld medical device may include a step of providing an inner drive shaft, an elongated, tubular, outer housing encapsulating the inner drive shaft such that the inner drive shaft is configured to be positioned within the outer housing, an implement at a distal end of the outer housing, wherein the inner drive shaft includes one or more inner drive shaft bendable sections positioned between distal and proximal ends of the inner drive shaft, wherein the outer housing includes one or more outer housing bendable sections positioned between distal and proximal ends of outer housing. The method may also include a step of heating the inner drive shaft. The method may include a step of inserting the inner drive shaft bendable section into the outer housing bendable section. The method may include the step of bending the inner drive shaft bendable section and the outer housing with a bender configured to bend the inner drive shaft bendable section and the outer housing bendable section. The step of bending may include bending with a bender including first and second arms coupled together via a pivot pin, whereby the first arm includes a first curved shaft receiver, and the second arm includes a second curved shaft receiver that is aligned with the first curved shaft receiver. The step of heating may include heating the inner drive shaft bendable section to anneal the material forming the inner drive shaft bendable section. In the method, the inner shaft bendable section used may have a lower flexure modulus than a flexure modulus for the outer housing bendable section. In the method, the inner shaft bendable section used may be more flexible than the outer housing bendable section. In the method, the inner shaft bendable section used may have a lower modulus of elasticity than a modulus or elasticity for the outer housing bendable section.

An advantage of the handheld medical device is that the inner drive shaft bendable section retrains its bent configuration once bent so that during use the inner drive shaft bendable section does not bind against the outer housing bendable section.

Another advantage of the handheld medical device is that the inner drive shaft bendable section may be heated to enable the inner drive shaft bendable section to be easily bent.

Yet another advantage of the handheld medical device is that a bender may be used to bend the inner drive shaft or outer housing, or both, to a desired configuration.

These and other embodiments are described in more detail below.

BRIEF DESCRIPTION OF THE FIGURES

FIG. 1 is a perspective view of a handheld medical device with an implement including first and second jaws.

FIG. 2 is a side view of the inner drive shaft.

FIG. 3 is a side view of the inner drive shaft positioned within the outer housing, with a distal portion of the outer housing cut away to show the inner drive shaft bendable section positioned in the outer housing.

FIG. 4 is side view of the inner drive shaft positioned within the outer housing of FIG. 3 with the inner drive shaft bendable section bent while positioned within the outer housing.

DETAILED DESCRIPTION OF THE FIGURES

Figure 5:
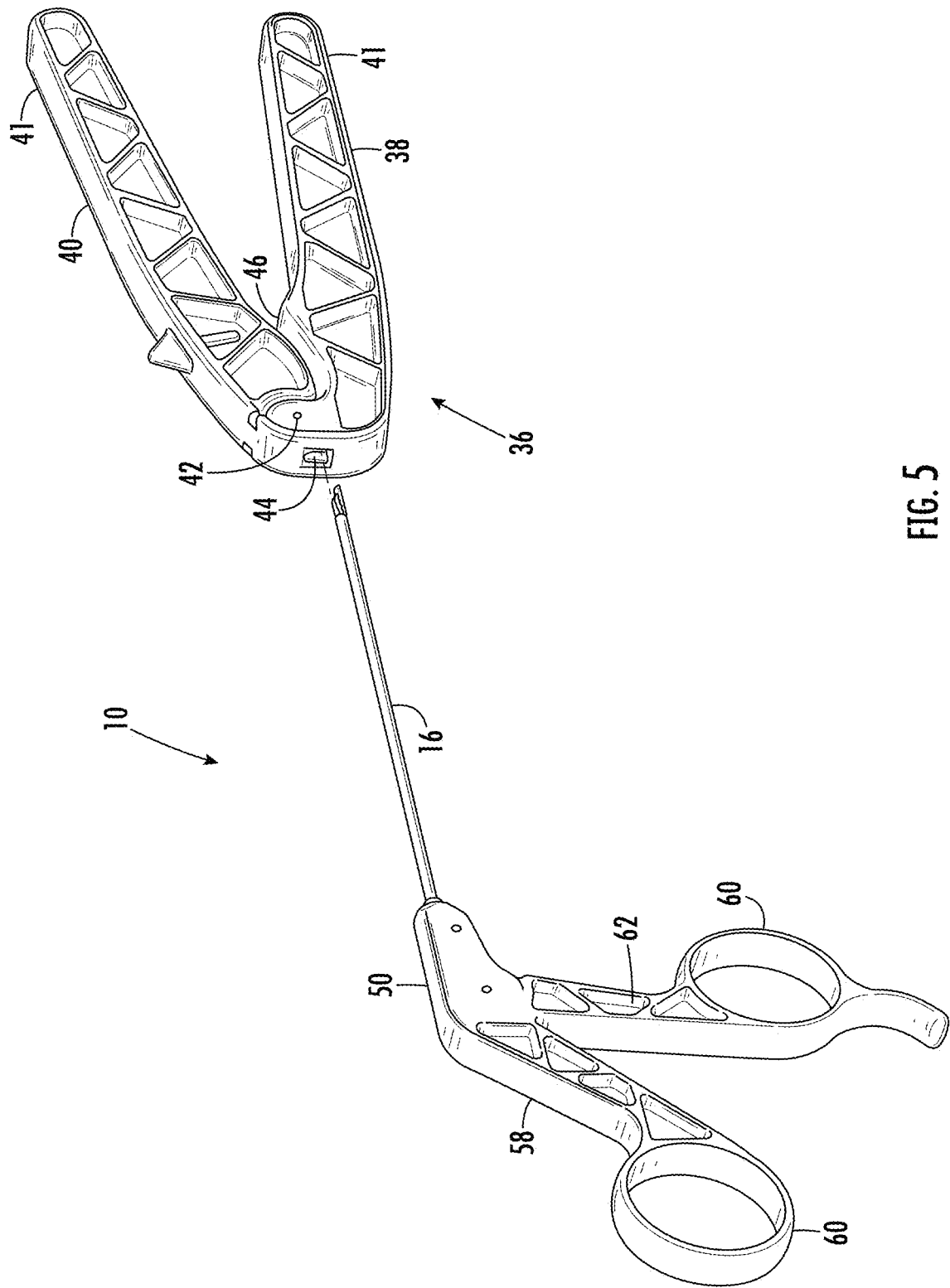
FIG. 5 is a perspective view of the handheld medical device and a bender used to bend the inner drive shaft bendable section.

As shown in FIGS. 1-7, a handheld medical device 10 with a distal implement 12 is disclosed. The handheld rotary medical device 10 may include an inner drive shaft 14, an elongated, tubular, outer housing 16 encapsulating the inner drive shaft 14 such that the inner drive shaft 14 is positioned within the outer housing 16. The inner drive shaft 14 may include one or more inner drive shaft bendable sections 18, and the outer housing 16 may include one or more outer housing bendable sections 20. The inner drive shaft bendable section 18 may be heated to anneal the material forming the inner drive shaft bendable section 18 such that during use, the inner drive shaft bendable section 18 may be bent into a desired position and, once bent, the inner drive shaft bendable section 18 remains in the desired position and does not bind against the elongated, tubular, outer housing 16.

The handheld medical device 10, as shown in FIGS. 1-3, may include the inner drive shaft 14 and the elongated, tubular, outer housing 16 encapsulating the inner drive shaft 14 such that the inner drive shaft 14 is positioned within the outer housing 16. An implement 12 may be positioned at a distal end 24 of the outer housing 16. The implement 12 may include first and second jaws 26, 28 that may be configured to open and close to grasp tissue and other objects. The first and second jaws 26, 28 may have any appropriate size, shape and configuration. The implement 12 may also be a burr, shaver or other desired tool.

The handheld medical device 10 may include the inner drive shaft 14 with one or more inner drive shaft bendable sections 18 positioned between distal and proximal ends 30, 32 of the inner drive shaft 14. The handheld medical device 10 may include the outer housing 16 with one or more outer housing bendable sections 20 positioned between distal and proximal ends 24, 34 of outer housing 16. The inner drive shaft bendable section 18 may be configured such that during use, the inner drive shaft bendable section 18 may be bent into a desired position and, once bent, the inner drive shaft bendable section 18 remains in the desired position and does not bind against the elongated, tubular, outer housing 16. Instead, the inner drive shaft bendable section 18 is positioned within the outer housing bendable section 20 but does not bind against the inner surface of the outer housing bendable section 20. Such configuration ensures that the implement 12 is easily actuated by a user, such as a surgeon.

The inner drive shaft bendable section 18, as shown in FIGS. 2-4, may be configured create an easy to use device for a surgeon. In at least one embodiment, the inner drive shaft bendable section 18 may be formed from materials, such as, but not limited to, stainless steel, such as stainless steel 17-7 and 17-4. The inner drive shaft bendable section 18 may be formed from a same material as a material forming the outer housing bendable section 20. Alternatively, the inner drive shaft bendable section 18 may be formed from different material than a material forming the outer housing bendable section 20.

In at least one embodiment, the inner drive shaft bendable section 18 may be formed from an annealed material enabling the inner drive shaft bendable section 18 to be bent, during use, as desired. The inner drive shaft bendable section 18 may be heated before being positioned within the outer housing bendable section 20. The inner drive shaft bendable section 18 may be heated to anneal the material forming the inner drive shaft bendable section 18, thereby making the inner drive shaft bendable section 18 more bendable. The inner drive shaft bendable section 18 may be heated to a temperature range between 1,900 degrees Fahrenheit and 2,000 degrees Fahrenheit for a period of time between two seconds and five seconds with a heating device, such as, but not limited to being, a heating/induction coil.

In at least one embodiment, the inner drive shaft bendable section 18 may be more bendable than the at least one outer housing bendable section 20 enabling the inner drive shaft bendable section 18 to be bent, during use, as desired. The inner drive shaft bendable section 18 has a lower flexure modulus than a flexure modulus for the outer housing bendable section 20 enabling the inner drive shaft bendable section 18 to be bent, during use, as desired. The inner drive shaft bendable section 18 may be more flexible than the outer housing bendable section 20. The inner drive shaft bendable section 18 may have a lower modulus of elasticity than a modulus or elasticity for the outer housing bendable section 20 enabling the inner drive shaft bendable section 18 to be bent, during use, as desired.

The inner drive shaft bendable section 18 may be formed at any desired point along a length of the inner drive shaft 14. In at least one embodiment, the inner drive shaft bendable section 18 within a distal third of the inner drive shaft 14. In other embodiments, the inner drive shaft bendable section 18 may be positioned in other positions. The inner drive shaft bendable section 18 may have any appropriate and desired length. The outer housing 16 supports the inner shaft 14 within the outer housing 16. The outer housing 16 also supports the inner drive shaft bendable section 18 within the outer housing 16 so that the inner drive shaft 14 can be supported enough inside the tube to allow the implement 12 to function properly.

The handheld medical device 10 may be any device configured to support the inner drive shaft 14 and outer housing 16. In at least one exemplary embodiment, the handheld medical device 10 may include a head 50 configured to support the inner drive shaft 14 and the outer housing 16. The inner drive shaft 14 and the outer housing 16 may be permanently or releasably attached to the head 50. The inner drive shaft 14 may include an attachment system 52 for enabling a proximal end of the inner drive shaft 14 to be attached to a handle arm. The attachment system 52 may include a slot 56 in the inner drive shaft 14 extending orthogonal to a longitudinal axis of the inner drive shaft 14 that is configured to receive a protrusion. The protrusion may be attached to a portion of a second arm 62 positioned within the head 50 to drive the inner drive shaft 14. The outer housing 16 may include an attachment system 54 enabling the outer housing 16 to be releasably attached to the head 50.

The handheld medical device 10 may include a first arm 58 extending proximally from the head 50. The first arm 58 may be positioned at an acute angle relative to a longitudinal axis of the inner drive shaft 14. The first arm 58 may be rigidly attached to the head 50, and, in at least one embodiment, may be formed unitarily with the head 50. The first arm 58 may include a digit receiver 60 thru which one or more digits of a human hand may extend to grasp the first arm 58.

The handheld medical device 10 may include a second arm 62 extending away from the head 50 and positioned between the first arm 58 and the inner drive shaft 14 and the outer housing 16. The second arm 62 may be pivotably coupled to the head 50 enabling the second arm 62 to be moved toward the first arm 58 and drive a protrusion on the second arm 62 within the head 50 towards the implement 12 at the distal end 24 of the outer housing 16. The second arm 62 may include a digit receiver 60 thru which one or more digits of a human hand may extend to grasp the second arm 62. As such, as user may squeeze the second arm 62 towards the first arm 58 to cause the protrusion on the portion of the second arm within the head 50 and on the other side of the pivot point to advance the inner drive shaft 14 distally along the longitudinal axis of the inner drive shaft 14.

Figure 7:
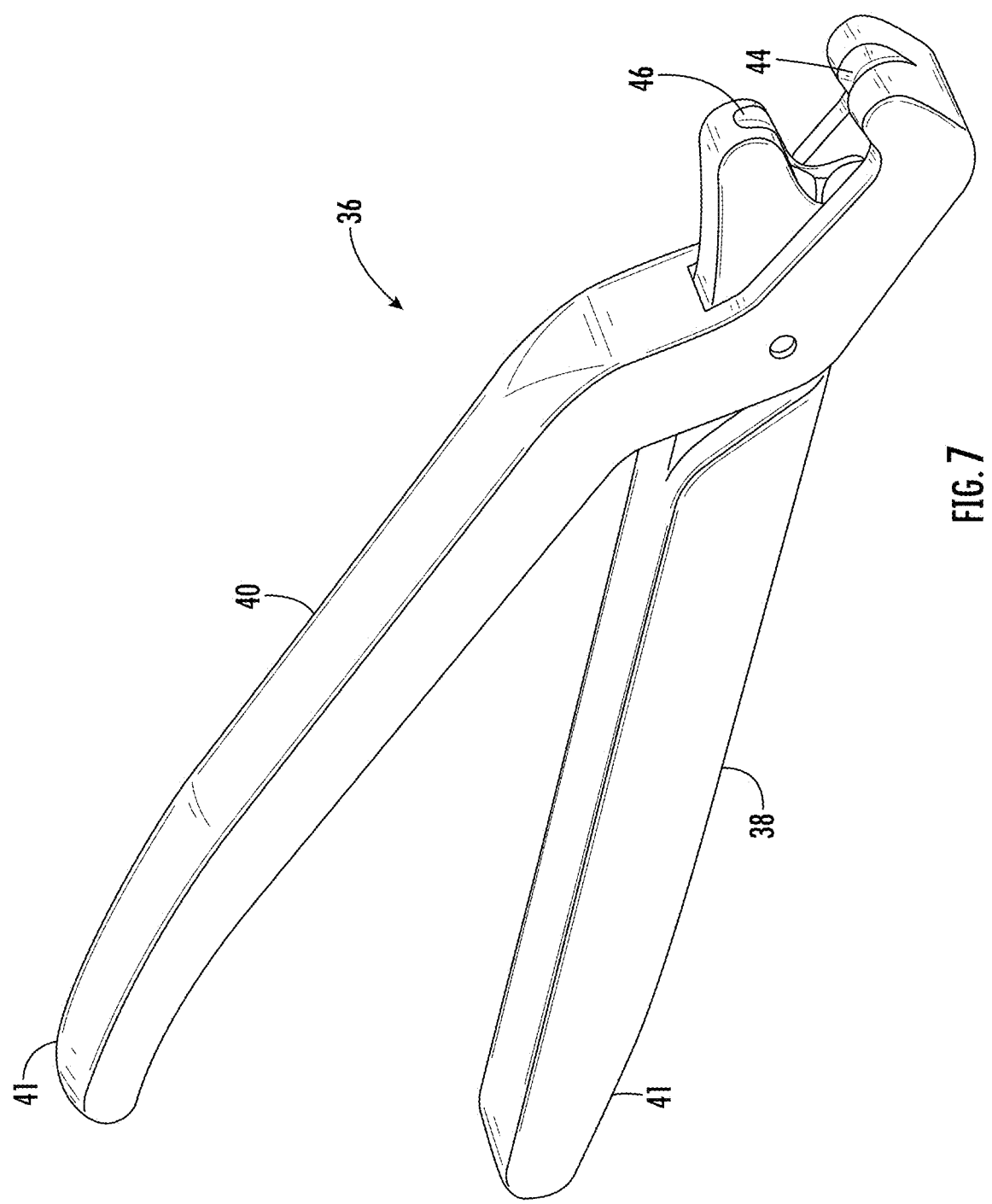
FIG. 7 is a perspective view of another embodiment of a bender used to bend the inner drive shaft bendable section.

The handheld medical device 10, as shown in FIGS. 5 and 7, may also include a bender 36 configured to bend the inner drive shaft bendable section 18 and the outer housing bendable section 20. The bender 36 may include first and second arms 38, 40 coupled together via a pivot pin 42. The first arm 38 may include a first curved shaft receiver 44. The second arm 40 includes a second curved shaft receiver 46 that is aligned with the first curved shaft receiver 44. The first and second curved shaft receivers 44, 46 may each have a groove that generally mirrors the shape of the inner drive shaft bendable section 18 and the outer housing bendable section 20. The bender may be configured to bend the inner drive shaft bendable section 18 and the outer housing bendable section 20 for 15° up, left or right bends, and even combination bends, such as, but not limited to 7.5° up+7.5° left/right. In the embodiment shown in FIG. 7, portions of the first and second arms 38, 40 extend past the pivot pin 42 where the position of the first and second arms 38, 40 relative to each other are inverted. In addition, the position of the first and second curved shaft receivers 44, 46 are on the opposite side of the pivot pin 42 relative to the handle portions 41. In contrast, the embodiment shown in FIG. 5 shows the first and second curved shaft receivers 44, 46 on the same side of the pivot pin 42 relative to the handle portions 41 of the first and second arms 38, 40.

During use, the inner drive shaft bendable section 18 or the outer housing bendable section, or the inner drive shaft bendable section 18 positioned within the outer housing bendable section 20 may be inserted into the first and second curved shaft receivers 44, 46. A user may squeeze the first and second arms 38, 40 towards each other to bend the inner drive shaft bendable section 18 or the outer housing bendable section, or both, as desired to suit the patient.

Figure 6:
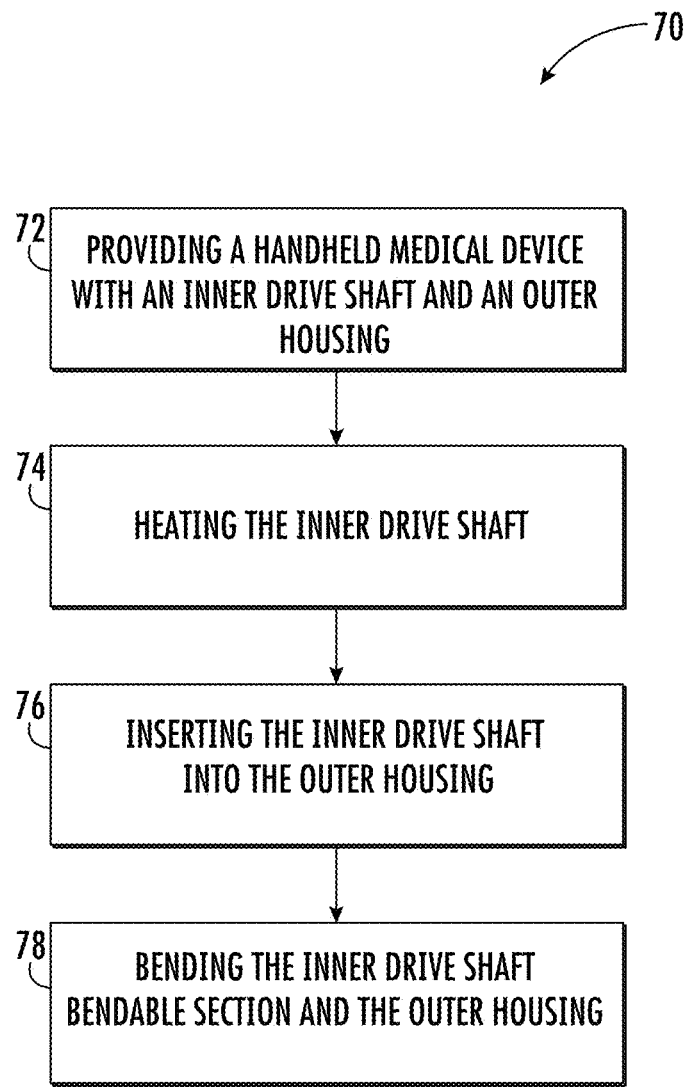
FIG. 6 is a flow chart of a method of forming the handheld medical device.

A method 70 of forming the handheld medical device 10 is shown in FIG. 6. The method 70 may include providing at 72 the handheld medical device 10. The handheld medical device 10 may include features as previously set forth, such as, but not limited to, the inner drive shaft 14, the elongated, tubular, outer housing 16 encapsulating the inner drive shaft 14 such that the inner drive shaft 14 is positioned within the outer housing 16, the implement 12 at the distal end 24 of the outer housing 16, whereby the inner drive shaft 14 may include one or more inner drive shaft bendable sections 18 positioned between distal and proximal ends 30, 32 of the inner drive shaft 14 and the outer housing 16 includes one or more outer housing bendable sections 20 positioned between distal and proximal ends 24, 34 of outer housing 16. The method 70 may include heating at 74 the inner drive shaft 14. Heating at 74 the inner drive shaft bendable section 18 anneals the material forming the inner drive shaft bendable section 18. The method 70 may also include inserting at 76 the inner drive shaft bendable section 18 into the outer housing bendable section 20.

The method 70 may include bending at 78 the inner drive shaft bendable section 18 and the outer housing 16 with a bender 36 configured to bend the inner drive shaft bendable section 18 and the outer housing bendable section 20. The bender 36 may be formed from first and second arms 38, 40 coupled together via a pivot pin 42. The first arm 38 of the bender 36 may include a first curved shaft receiver 44, and the second arm 40 may include a second curved shaft receiver 46 that is aligned with the first curved shaft receiver 44. Bending at 78 the inner drive shaft bendable section 18 may include an inner drive shaft bendable section 18 that has a lower flexure modulus than a flexure modulus for the outer housing bendable section 20. Bending at 78 the inner drive shaft bendable section 18 may include an inner drive shaft bendable section 18 that is more flexible than the outer housing bendable section 20. Bending at 78 the inner drive shaft bendable section 18 may include an inner drive shaft bendable section 18 that has a lower modulus of elasticity than a modulus or elasticity for the outer housing bendable section 20.

During use, the handheld medical device 10 may be used by a surgeon in a straight configuration or in a bent configuration, or both. The surgeon may bend the one or more inner drive shaft bendable sections 18 and the one or more outer housing bendable sections 20. The surgeon may bend the sections 18, 20 with his hands, on an object, with use of the bender 36 or in another manner that enables the surgeon to achieve the desired shape. When in the bent state, the handheld medical device 10 is designed such that the inner drive shaft bendable section 18 remains bent and does not bind on an inner surface of the outer housing 16 or an inner surface of the outer housing bendable section 20.

The foregoing is provided for purposes of illustrating, explaining, and describing embodiments of the disclosed devices.

We claim:

1. A handheld medical device, comprising:
    an inner drive shaft;
    an elongated, tubular, outer housing encapsulating the inner drive shaft such that the inner drive shaft is positioned within the outer housing;
    an implement at a distal end of the outer housing;
    wherein the inner drive shaft includes at least one inner drive shaft bendable section positioned between distal and proximal ends of the inner drive shaft;
    wherein the outer housing includes at least one outer housing bendable section positioned between distal and proximal ends of outer housing;
    wherein the at least one inner drive shaft bendable section is more bendable than the at least one outer housing bendable section;
    a bender configured to bend the at least one inner drive shaft bendable section and the at least one outer housing bendable section; and
    wherein the bender comprises first and second arms coupled together via a pivot pin and wherein the first arm includes a first curved shaft receiver and the second arm includes a second curved shaft receiver that is aligned with the first curved shaft receiver.

2. The handheld medical device of claim 1, wherein the at least one inner drive shaft bendable section is formed from an annealed material.

3. The handheld medical device of claim 1, wherein the at least one inner drive shaft bendable section has been heated when positioned within the at least one outer housing bendable section.

4. The handheld medical device of claim 1, wherein the at least one inner drive shaft bendable section has a lower flexure modulus than a flexure modulus for the at least one outer housing bendable section.

5. The handheld medical device of claim 1, wherein the at least one inner drive shaft bendable section is more flexible than the at least one outer housing bendable section.

6. The handheld medical device of claim 1, wherein the at least one inner drive shaft bendable section has a lower modulus of elasticity than a modulus or elasticity for the at least one outer housing bendable section.

7. The handheld medical device of claim 1, wherein the implement at the distal end of the outer housing comprises first and second jaws.

8. The handheld medical device of claim 1, wherein the at least one inner drive shaft bendable section is formed within a distal third of the at least one inner drive shaft bendable section.

9. The handheld medical device of claim 1, wherein the at least one inner drive shaft bendable section is formed from a same material as a material forming the at least one outer housing bendable section.

10. A handheld device, comprising:
an inner drive shaft;
an elongated, tubular, outer housing encapsulating the inner drive shaft such that the inner drive shaft is positioned within the outer housing;
an implement at a distal end of the outer housing;
wherein the inner drive shaft includes at least one inner drive shaft bendable section positioned between distal and proximal ends of the inner drive shaft;
wherein the outer housing includes at least one outer housing bendable section positioned between distal and proximal ends of outer housing; and
wherein the at least one inner drive shaft bendable section is heated forming an annealed at least one inner drive shaft bendable section;
a bender configured to bend the at least one inner drive shaft bendable section and the at least one outer housing bendable section;
wherein the bender comprises first and second arms coupled together via a pivot pin and wherein the first arm includes a first curved shaft receiver and the second arm includes a second curved shaft receiver that is aligned with the first curved shaft receiver; and
wherein the at least one inner drive shaft bendable section is more flexible than the at least one outer housing bendable section.

11. The handheld medical device of claim 10, wherein the at least one inner drive shaft bendable section has been heated when positioned within the at least one outer housing bendable section.

12. The handheld medical device of claim 10, wherein the at least one inner drive shaft bendable section has a lower flexure modulus than a flexure modulus for the at least one outer housing bendable section.

13. The handheld medical device of claim 10, wherein the at least one inner drive shaft bendable section has a lower modulus of elasticity than a modulus or elasticity for the at least one outer housing bendable section.

14. The handheld medical device of claim 10, wherein the at least one inner drive shaft bendable section is formed within a distal third of the at least one inner drive shaft bendable section.

15. The handheld medical device of claim 10, wherein the at least one inner drive shaft bendable section is formed from a same material as a material forming the at least one outer housing bendable section.

* * * * *